United States Patent [19]

Bock, deceased

[11] 3,968,154

[45] July 6, 1976

[54] METHOD OF PRODUCING PENICILLAMINE

[75] Inventor: Manfred Klaus Joachim Bock, deceased, late of Berlin-Dahlem, Germany, by Ingrid Alida Anni Bock, heiress

[73] Assignee: Firma Heyl & Co. Chemisch-Pharmazeutische Fabrik, Berlin, Germany

[22] Filed: Oct. 29, 1974

[21] Appl. No.: 518,872

Related U.S. Application Data

[63] Continuation-in-part of Ser. No. 236,962, March 22, 1972, Pat. No. 3,894,067.

[30] Foreign Application Priority Data

Mar. 24, 1971 Germany............................ 2114329

[52] U.S. Cl. ............................................ 260/534 S
[51] Int. Cl.² ..................................... C07C 149/243
[58] Field of Search................................ 260/534 S

[56] References Cited
UNITED STATES PATENTS 3,281,461  10/1966  Restivo et al.................... 260/534 S

FOREIGN PATENTS OR APPLICATIONS 854,339  11/1960  United Kingdom ............. 260/534 S Primary Examiner—Richard L. Raymond
Attorney, Agent, or Firm—Steinberg and Blake

[57] ABSTRACT

This invention relates to the production of penicillamine and acid addition salts of penicillamine through the production from penilloic acid or penicilloic acid formed by hydrolytic decomposition of a penicillin of penicillamine-mercuric-mercaptide which can be easily decomposed by means of hydrogen sulfide to penicillamine. The penicillamine-mercuric-mercaptide is formed as a crystalline precipitate by reaction of the penicilloic acid or penilloic acid with a mercuric salt in a ratio of 1:0.5 in a medium of a water miscible organic solvent and the precipitated penicillamine-mercuric-mercaptide after separation from the reaction medium is decomposed to the penicillamine.

9 Claims, No Drawings

METHOD OF PRODUCING PENICILLAMINE

CROSS REFERENCE TO RELATED APPLICATION

This application is a continuation-in-part of application Ser. No. 236,962, filed Mar. 22, 1972, for "Production of Penicillamine-Mercuric-Mercaptide and of Penicillamine and Acid Addition Salts of Penicillamine," now U.S. Pat. No. 3,894,067.

BACKGROUND OF THE INVENTION

The production of the penicillamine by the hydrolytic decomposition of penicillin is known.

According to British Pat. No. 854,339, penicillins are converted by alkaline hydrolysis into the corresponding penicilloic acid. This is then isolated after extraction with an organic solvent such as n-butanol and by decarboxylation at increased temperature under lowered pressure converted into the corresponding penilloic acid.

The sodium salt of the penilloic acid is reacted with a mercuric halogenide, for example mercuric chloride, or a mercuric salt in the presence of halogen ions in aqueous solution. This results in the formation of a penicillamine-mercuric-halogenide-complex compound which is isolated by filtration and then thoroughly freed from the formed by-product penilloaldehyde and the inorganic salt by washing and suspending.

The complex is suspended in water and reacted with hydrogen sulfide. The mercury sulfide precipitates and is filtered off. The filtrate is concentrated by drying under vacuum. Penicillamine-hydrochloride is thus obtained. This is reacted with acetone for purification purposes. This results in the formation of penicillamine-isopropylidine-hydrochloride which is again converted to penicillamine-hydrochloride by means of a mineral acid such as hydrochloric acid at increased temperature.

In accordance with U.S. Pat. No. 3,281,461, a penicillin is hydrolized in alkaline medium to the corresponding penicilloic acid which, by means of a strong acid such as hydrochloric acid, is decarboxylated to the corresponding penilloic acid. By the reaction of the penilloic acid with mercuric chloride as the mercury (II)-salt, there is thus obtained the mercuric chloride complex of the penicillamine which is kept in solution.

The main interfering by-product is a penilloaldehyde, which, if not removed prior to the conversion of the mercuric complex, greatly reduces the recoverable yield of penicillamine. This removal can be accomplished by extraction by means of an organic solvent such as chloroform, ethyl acetate or methylene chloride, or by reaction with a carbonyl-group-containing reagent such as hydroxylamine, semicarbazide or hydrazine. This compound forms with the penilloaldehyde an insoluble derivative at increased temperature which after renewed addition of mineral acid is filtered.

The solution freed from the penilloaldehyde is reacted with hydrogen sulfide, the resulting mercury sulfide is filtered off and the filtrate mixed with an organic solvent such as a short chain ester or alcohol, and the water is then removed by distillation. There is thus obtained crude penicillamine-hydrochloride. This can be purified through formation of the isopropylidene-derivative by reaction with acetone, and the said derivative decomposed with hydrochloric acid.

The known methods exhibit several disadvantages. In the first place it is necessary to operate with large volumes of reaction solutions since the utilized mercury compounds are relatively insoluble in water. Furthermore, it is necessary to operate with a mol ratio of mercury compound to penicilloic acid or penilloic acid of at least 1:1. This means that relatively large amounts of the mercury compounds must be utilized. This is disadvantageous, since the mercury compounds are expensive throughout the world.

SUMMARY OF THE INVENTION

Generally speaking, in accordance with the present invention, a method is provided which utilizes smaller amounts of mercury compounds and which avoids the disadvantages of the known processes for the production of penicillamine and acid addition salts thereof.

It is accordingly a primary object of the present invention to provide a method of producing D-penicillamine and acid addition salts thereof, which method can utilize considerably smaller amounts of liquid volumes for the reaction solutions and which also utilizes smaller amounts of mercury compounds.

It is another object of the present invention to provide for the production of penicillamine-mercuric-mercaptide as a crystalline precipitate which can easily be separated from the reaction solution and which, after separation can easily be decomposed to penicillamine, whereby high yields of penicillamine are obtained.

Other objects and advantages of the present invention will be apparent from a further reading of the specification and of the appended claims.

With the above and other objects in view, the present invention mainly comprises the production of penicillamine by reacting penilloic acid or penicilloic acid with a concentrated solution of a mercuric salt in a water miscible organic solvent, preferably methanol, ethanol, acetone or methanol/acetone in a 1:1 ratio, in a mol ratio of penilloic acid or penicilloic acid to mercuric salt of 1:03 – 1:07, preferably 1:0.5, whereby crystalline penicillamine-mercuric-mercaptide is formed in which both valences of the divalent mercuric are bound to penicillamine residues, (the ratio of penicillamine to mercury thus being 2:1) the crystalline penicillamine-mercuric-mercaptide precipitating from the solution and therefore being easily separated therefrom, and then converted to penicillamine by means of hydrogen sulfide.

It is preferred to use a 1 to 2 molar methanolic or methanolic/acetone solution of mercuric chloride for reaction with the penilloic acid or penicilloic acid so that the formed penicillamine-mercuric-mercaptide is easily precipitated from the solution.

The method of the present invention utilizes considerably smaller volumes of liquid in the reaction solutions, as little as one-tenth of that required according to known processes. This is achieved as a result of the following considerations:

At 20°C, one can dissolve 50 g of mercuric chloride in 100 g of alcohol, as compared to only 7.4 g of mercuric chloride in 100 g of water. Thus, it is possible to operate with a concentrated solution and smaller volumes are also possible since the mol ratio of the reactants according to the invention is lower than mol ratios according to known processes.

A particular advantage of the present process resides in the fact that the initial product of the process, the produced penicillamine-mercuric-mercaptide complex compound precipitates in crystalline form and is easily separated from the reaction solution. The major interfering by-product of the process, namely penilloaldehyde, however, remains dissolved in the solution and therefore can not interfere with the further working up of the complex compound to penicillamine.

The penicilloic acid or penilloic acid which is reacted with the mercuric salt in a mol ratio of 1:0.3 – 1:0.7, preferably 1:0.5 may be obtained from any source, for example a. penicilloic acid obtained as an intermediate during hydrolysis of penicillin, or b. penilloic acid obtained by decarboxylation of penicilloic acid.

The organic solvent which is utilized for preparing the mercuric salt solution in the method of the invention should be a water miscible organic solvent. Most suitable for this purpose are methanol, ethanol, acetone or a methanol/acetone mixture (1:1).

The penicillamine-mercuric-mercaptide is decomposed, if necessary, in acid medium by means of hydrogen sulfide, to penicillamine, and the penicillamine-containing solution is evaporated to dryness under vacuum.

It is suitable to carry out the reaction calculated with respect to the number of base equivalents, since the number of acid functions of the penicilloic acid or penilloic acid correspond. In order to obtain the suitable intermediate penicillamine-mercuric-mercaptide wherein each of the two valences of the mercuric ion is bound to a penicillamine residue, it is necessary to utilize a mol ratio of penicilloic acid or penilloic acid to mercuric compound of 1:03–1:07, preferably 1:0.5.

The penicillamine-mercuric-mercaptide is a 2:1 complex (penicillamine:mercuric). This substance exhibits the advantage as compared to the known complex compounds of being more easily separable and decomposable and contains only one-half the amount of mercury and it therefore serves as a most suitable intermediate for the production of the penicillamine.

As indicated above, the penilloaldehyde which could interfere with the production of penicillamine remains as acetal in solution and can without particular difficulty be separated from the crystalline precipitated penicillamine-mercuric-mercaptide by filtration and removed from the residue by washing with aqueous alcohol.

It is still a further advantage of the present invention that the penicillamine-mercuric-mercaptide which is produced according to the invention can be recrystallized from water in simple manner. A method step of this type is not possible in the case of the complex formation which occurs in the known processes.

To further work up the penicillamine-mercuric-mercaptide which is produced according to the present invention, the same is suspended in water or an organic solvent. Hydrogen sulfide is then introduced. The precipitated mercuric sulfide is filtered off, and to increase the yield penicillamine is washed out of the same. The washing liquor is purified along with the main filtrate which contains the penicillamine. The penicillamine is obtained by evaporation of the filtrate under vacuum.

The base is thus directly obtained, which is a particular advantage as compared to the prior art which only results in the obtaining of the penicillamine hydrochloride. If it is desired to obtain the penicillamine hydrochloride in the method of the present invention, then the mercaptide is worked up in accordance with the invention in hydrochloric acid solution. The mercaptide is dissolved in hydrochloric acid and the process proceeds as previously described. Evaporation of the filtrate results in the obtaining of the penicillamine hydrochloride. This can be reconverted to the penicillamine base by reaction of the hydrochloride with a suitable base such as dimethylamine in alcoholic solution. The penicillamine base is obtained in crystalline form.

It should further be noted that the method of the present invention differs from the known methods in that the method of the invention can proceed starting not only with penilloic acid, but also its precursor, namely with penicilloic acid.

DESCRIPTION OF PREFERRED EMBODIMENTS

The following examples are given to further illustrate the present invention. The scope of the invention, is not, however, meant to be limited to the specific details of the examples.

EXAMPLE 1 a. Production of Penicillamine-Mercuric-Mercaptide from Intermediate Penicilloic Acid 372 g of the potassium salt of penicillin-G (1 mol) are dissolved in 250 cc of water and 180 cc of 20% aqueous sodium hydroxide solution. This results in an increase in the temperature to 60°–70° C. After one-half hour 8.3 cc of concentrated hydrochloric acid of 1.19 density is added thereto. Then a mixture of 250 cc of 1 molar methanolic mercuric chloride solution and 83 cc of concentrated hydrochloric acid of 1.10 density are added dropwise under stirring, resulting in a decarboxylation. An additional 250 cc of 1 molar methanolic mercuric chloride solution are added thereto, resulting in the separation of crystalline penicillamine-mercuric-mercaptide. The mercaptide is filtered off under suction, washed with 200 cc of 50% methanol and dried. There is thus obtained 194 g (78% of the theoretical) of penicillamine-mercuric-mercaptide.

b. Conversion of the Mercaptide to Penicillamine 248 g of penicillamine-mercuric-mercaptide (½ mol) is suspended in 1.2 liters of water. There is then added 1 cc of hydrochloric acid to improve the filterability of the sulfide precipitate. After the introduction of hydrogen sulfide, the precipitated mercury sulfide is filtered off and washed with 0.8 liters of water. The washing liquid is combined with the main filtrate and this is then evaporated to dryness.

There is thus obtained 118 g of penicillamine, corresponding to 79% of the theoretical.

c. Conversion of the Mercaptide to Penicillamine-Hydrochloride 248 g of penicillamine-mercuric-mercaptide (½ mol) are dissolved in 500 cc of water and 83 cc of concentrated hydrochloric acid of 1.19 density. After the introduction of hydrogen sulfide, the precipitated mercury sulfide is filtered off and washed with 1 liter of water. The washing liquor is combined with the main filtrate and this is evaporated to dryness under vacuum.

There is thus obtained 182 g of penicillamine-hydrochloride, corresponding to 98% of the theoretical.

d. Conversion of Penicillamine-Hydrochloride Into Penicillamine Base

The hydrochloride obtained according to (c) above is dissolved in 250 cc of methanol, the solution filtered and the pH thereof adjusted to 3 with 80 cc of 40% aqueous dimethylamine solution. After the start of the crystallization an additional 35 cc of dimethylamine solution is added, the pH value increases to 4.5. The 50° C warm mixture is then cooled to about 0°–5° C. The course, glistening crystals are filtered off under suction, washed with 150 cc of 90% methanol and dried.

There is thus obtained 100 g of penicillamine, corresponding to 67 percent of the theoretical. The purity is greater than 99 percent.

EXAMPLE 2

Production of Penicillamine-Mercuric-Mercaptide from Intermediate Penilloic Acid a. 372 g of the potassium salt of penicillin-G (1 mol) are dissolved in 200 cc of water and 180 cc of 20% aqueous sodium hydroxide solution, resulting in warming to 60°–70° C. After one-half hour there is then slowly added dropwise and under stirring 100 cc of concentrated hydrochloric acid of 1.19 density at 80° C. After the termination of the decarboxylation, 16.5 cc of 20% aqueous sodium hydroxide solution are added. After cooling there is subsequently added dropwise 500 cc of 1 molar methanolic mercuric chloride solution. This results in the precipitation of crystalline penicillamine-mercuric-mercaptide. This is washed with 200 cc of 50% methanol and dried. There is thus obtained 203 g of penicillamine-mercuric-mercaptide, which corresponds to 81% of the theoretical.

b. Instead of using the potassium salt of penicillin-G, the process is carried out with 356 g of the sodium salt of penicillin-G (1 mol), resulting in the same yield of penicillin-mercuric-mercaptide.

EXAMPLE 3

Production of Penicillamine-Mercuric-Mercaptide from Penilloic Acid a. 326 g of benzylpenilloic acid-hydrate (1 mol) are dissolved in 250 cc of water and 168 cc of 20% aqueous sodium hydroxide solution and reacted under stirring slowly with 500 cc of 1 molar methanolic mercuric chloride solution.

The precipitated crystals of penicillamine-mercuric-mercaptide are filtered off under suction, washed with 200 cc of 50% methanol and dried.

There is thus obtained 244 g of penicillamine-mercuric-mercaptide, which corresponds to 98% of the theoretical.

b. 250 cc of a 2-molar solution of mercuric chloride in methanol-acetone (1:1) are utilized. There is thus obtained 174 g of penicillamine-mercuric-mercaptide, which corresponds to 70% of the theoretical.

Although methanol, ethanol and acetone, as well as a methanol-acetone mixture have been mentioned as preferred solvents, other suitable water miscible solvents for the purposes of the present invention include dimethylformamide, dimethylsulfoxide, n-propanol, isopropanol and methylethyl ketone.

It is also possible to use a mixture of organic solvent and water, in which case the ratio of organic solvent and water in such medium is preferably between 1:3 and 3:1, the most preferred ratio being 1:1.

The method of the invention can of course be carried out with other mercuric salts than mercuric chloride and mercuric acetate. Among such salts are the other mercuric halides, e.g. mercuric bromide and mercuric iodide, as well as mercuric salts of organic acids such as mercuric formate and mercuric propionate.

It should further be noted that in accordance with a preferred embodiment of the present invention the mercuric salt, preferably mercuric chloride is used in the form of a 1 molar solution to facilitate the precipitation of the penicillamine-mercuric-mercaptide.

While the invention has been illustrated in particular with respect to specific reactants and reaction conditions, it is apparent that variations and modifications can be made without departing from the spirit and scope of the invention.

What is claimed is:

1. Method of producing penicillamine, which comprises reacting a compound selected from the group consisting of penicilloic acid and penilloic acid with a mercuric salt in a mol ratio of 1:0.3 – 1:0.7 in a medium of at least one water miscible organic solvent and water in a ratio of organic solvent to water of between about 1:3 and 3:1, thereby forming penicillamine-mercuric-mercaptide in crystalline form which precipitates in such form from the solution and penilloaldehyde as by-product which remains dissolved in the solution, separating and precipitated crystalline penicillamine-mercuric-mercaptide from the solution containing the by-product, and decomposing said penicillamine-mercuric-mercaptide to form penicillamine.

2. Method according to claim 1 wherein said penicillamine-mercuric-mercaptide is reacted with hydrogen sulfide to form penicillamine.

3. Method according to claim 2 wherein the reaction with hydrogen sulfide is carried out in acid medium to form the corresponding acid addition salt of penicillamine.

4. Method according to claim 1 wherein said water miscible organic solvent is selected from the group consisting of methanol, ethanol, acetone and a methanol/acetone 1:1 mixture.

5. Method according to claim 1 wherein said mercuric salt is mercuric chloride.

6. Method according to claim 5 wherein said mercuric chloride is in a 1 molar solution in said water miscible organic solvent.

7. Method according to claim 6 wherein said water miscible organic solvent is methanol.

8. Method according to claim 1 wherein said decomposition of said penicillamine-mercuric-mercaptide is carried out in a medium including a pharmaceutically acceptable acid, whereby the corresponding pharmaceutically acceptable acid addition salt of penicillamine is formed.

9. Method according to claim 1 wherein the ratio of said compound to said mercuric salt is 1:0.5.

* * * * *